(12) United States Patent
Di Emidio

(10) Patent No.: US 6,290,497 B1
(45) Date of Patent: Sep. 18, 2001

(54) SURGICAL INSTRUMENT USED TO DRILL PARALLEL HOLES IN DENTAL IMPLANTS

(75) Inventor: Paolo Di Emidio, Controquerra (IT)

(73) Assignee: Piergiacomi Sud_S.R.L. (IT)

( * ) Notice: Subject to any disclaimer, the term of this patent is extended or adjusted under 35 U.S.C. 154(b) by 0 days.

(21) Appl. No.: 09/608,726

(22) Filed: Jun. 30, 2000

(30) Foreign Application Priority Data

Jul. 6, 1999 (IT) .............................................. AN99A0034

(51) Int. Cl.[7] ...................................................... A61C 3/02
(52) U.S. Cl. ................................................................ 433/76
(58) Field of Search ....................................................... 433/76

(56) References Cited

U.S. PATENT DOCUMENTS

| 1,387,329 | * | 8/1921 | Stark ....................................... 433/76 |
| 4,344,755 | * | 8/1982 | Gold et al. ............................... 433/76 |

* cited by examiner

*Primary Examiner*—John J. Wilson
(74) *Attorney, Agent, or Firm*—Leonard Bloom

(57) ABSTRACT

The present invention concerns a surgical instrument used to drill parallel holes in dental implants, comprising a handle on which a rod with a series of small spheres is screwed, with the ability for tightening a pair of small plates on each sphere in order to support an element ending with a guide head, with calibrated hole, for the milling cutter used to drill holes in dental implants.

1 Claim, 2 Drawing Sheets

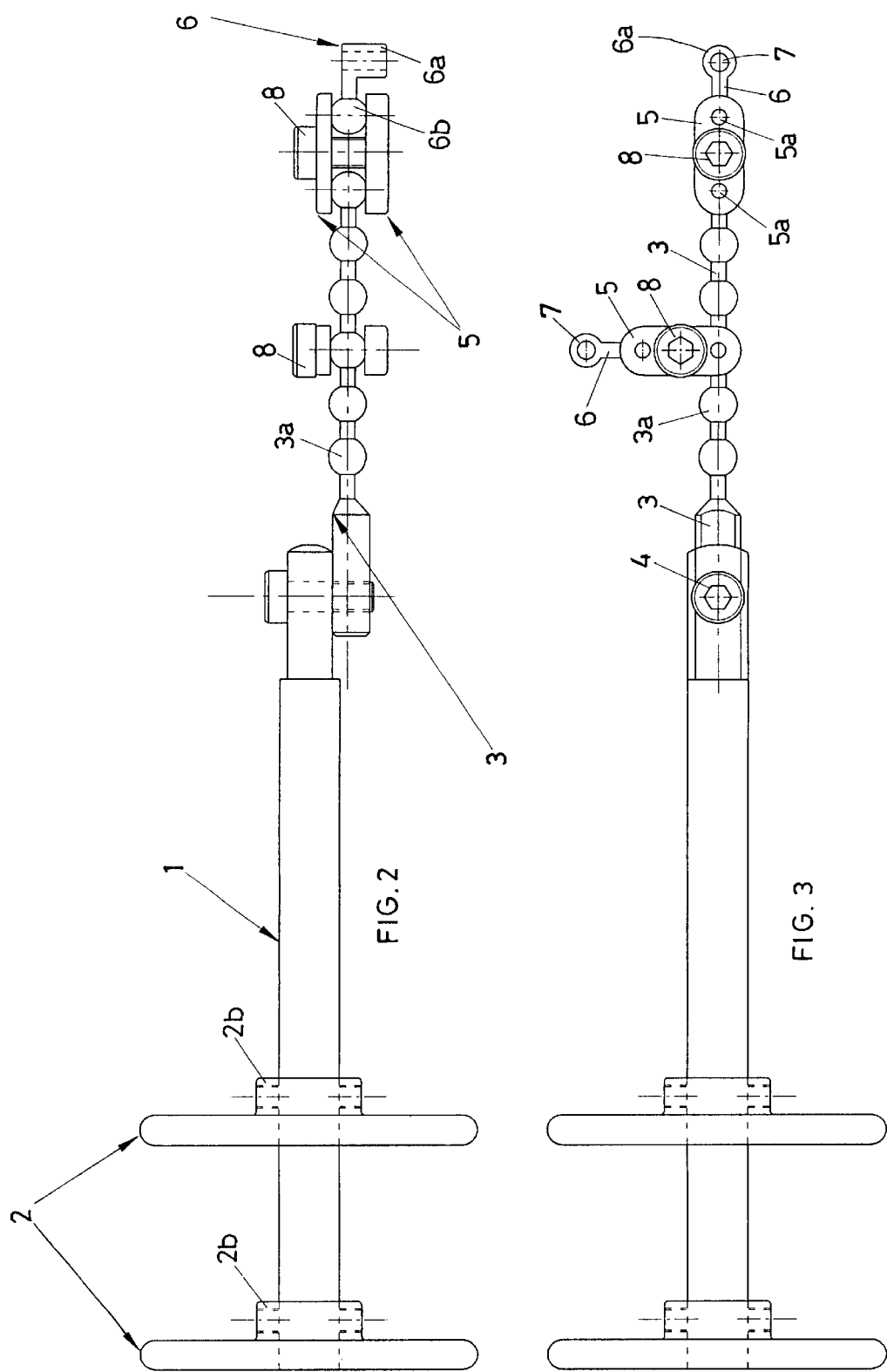

SURGICAL INSTRUMENT USED TO DRILL PARALLEL HOLES IN DENTAL IMPLANTS

BACKGROUND OF THE INVENTION

1. Field of the Invention

The present patent application for industrial invention concerns a surgical instrument used to drill parallel holes in dental implants.

2. Description of Related Art

More precisely, the use of the instrument according to the present invention allows for drilling perfectly parallel holes in bony seats, such a maxillary, mandibular and/or other seats (epithesis), during the preparatory stage to the surgical incorporation of osteo-integrated dental implants.

Biomechanics plays a very important role in dental implantation where the parallelism between two or more implant elements with respect to the occlusion plane is crucial. Therefore, an incorrect design disregarding the biomechanic principle of implant-prosthetic reconstruction could result in overload reactions with perimplant osseous reabsorption and consequent loss of the osteo-integrated implant during the following clinical stage.

As a matter of fact, in the presence of implant disparallelism, the force vector (masticatory load) acting on the osteo-integrated implant will generate a rotary movement that affects the individual load of the perimplant osseous tissue.

Currently, the most popular parallelization system for the holes drilled in implant beds makes use of a surgical guide resin plate. This system, however, is not capable of ensuring implant parallelism.

Moreover, such a system does not allow for suitably capturing the osseous plane and does not provide good fixing during the drilling of the master hole.

On the contrary, the use of the surgical instrument according to the present invention will guarantee the following results:

- suitable reaching of the osseous plane in the intraoperative stage;
- parallelism of the osseous master holes;
- perfect correspondence of the master holes with the center of the occlusion surfaces;
- good visibility of the operative field;
- ergonomics of the surgical operation.

It must be noted that the use of the surgical instrument according to the present invention is indefinite in time, since it can be reused again and again after being sterilized in the autoclave.

The surgical instrument according to the present invention comprises a handle on which a close pair of disks is fixed at an adjustable distance. The end of the handle is pivoted on a second rod characterized in that it features a series of regularly spaced small spheres.

SUMMARY OF THE INVENTION

The instrument according to the present invention is provided with two or more identical pairs of plates, each of them acting as support for an element ending with a head with calibrated hole.

The pairs of plates can be tightened and adjusted in their stop position on each of the small spheres of the second rod. Each element is tightened and adjusted in its blocking position within the corresponding pair of support plates.

The double adjustment allows for orientating and fixing the heads with calibrated holes in any direction at any distance.

The two pairs of plates can be fixed closer or farther with respect to the pivoting point of the second rod that, in turn, can be held in place with any inclination angle with respect to the first rod.

The great articulation of the surgical instrument according to the present invention is extremely important in order to reach and operate with maximum comfort and efficiency in any point of the maxilla or mandible. At the same time, the surgeon will be able to set the most convenient spatial configuration of the instrument for him in terms of instrument grip or surgical technique.

A brief description of the operation modes both during the laboratory preliminary stage and in the surgical stage will allow for better understanding the advantages of the instrument according to the present invention.

A surgical guide resin plate is created from the plaster models mounted on articulator at mean values. Holes are drilled in the centre of the occlusion surfaces, according to the known technique.

The fenestration of the surgical guide plate is realised in vestibular or palatar seat according to the known surgical technique. The distance between the holes is determined and fixed using an ordinary caliper and transferred onto the holes of the heads of the elements of the instrument according to the present invention.

Once the element-supporting plates are tightened onto the second rod, the second rod is orientated in the most convenient position in order to facilitate the surgical access and fixed to the first rod.

In the surgical stage the fenestrated surgical guide plate is transferred together with the instrument according to the present invention, after blocking the heads in a suitable position.

The surgical milling cutter will be housed in the head holes to realise the master hole with reference to the centre of the occlusion surface of the resin plate.

Once the master hole has been drilled, the blocking pin to be inserted in one of the calibrated holes of the elements of the instrument according to the present invention is introduced into the master hole in order to use the blocking pin as fixed reference point for the correct drilling of all the other holes, by inserting the milling cutter into the calibrated holes of all the elements of the second rod of the instrument.

For major clarity the description of the surgical instrument according to the present invention continues with reference to the enclosed drawings, which are intended for purposes of illustration and not in a limiting sense, whereby:

BRIEF DESCRIPTION OF THE DRAWINGS

FIG. 2 is a side view of the surgical instrument according to the present invention.

FIG. 3 is an orthogonal projection of FIG. 1.

DESCRIPTION OF THE PREFERRED EMBODIMENTS

Figure 1:
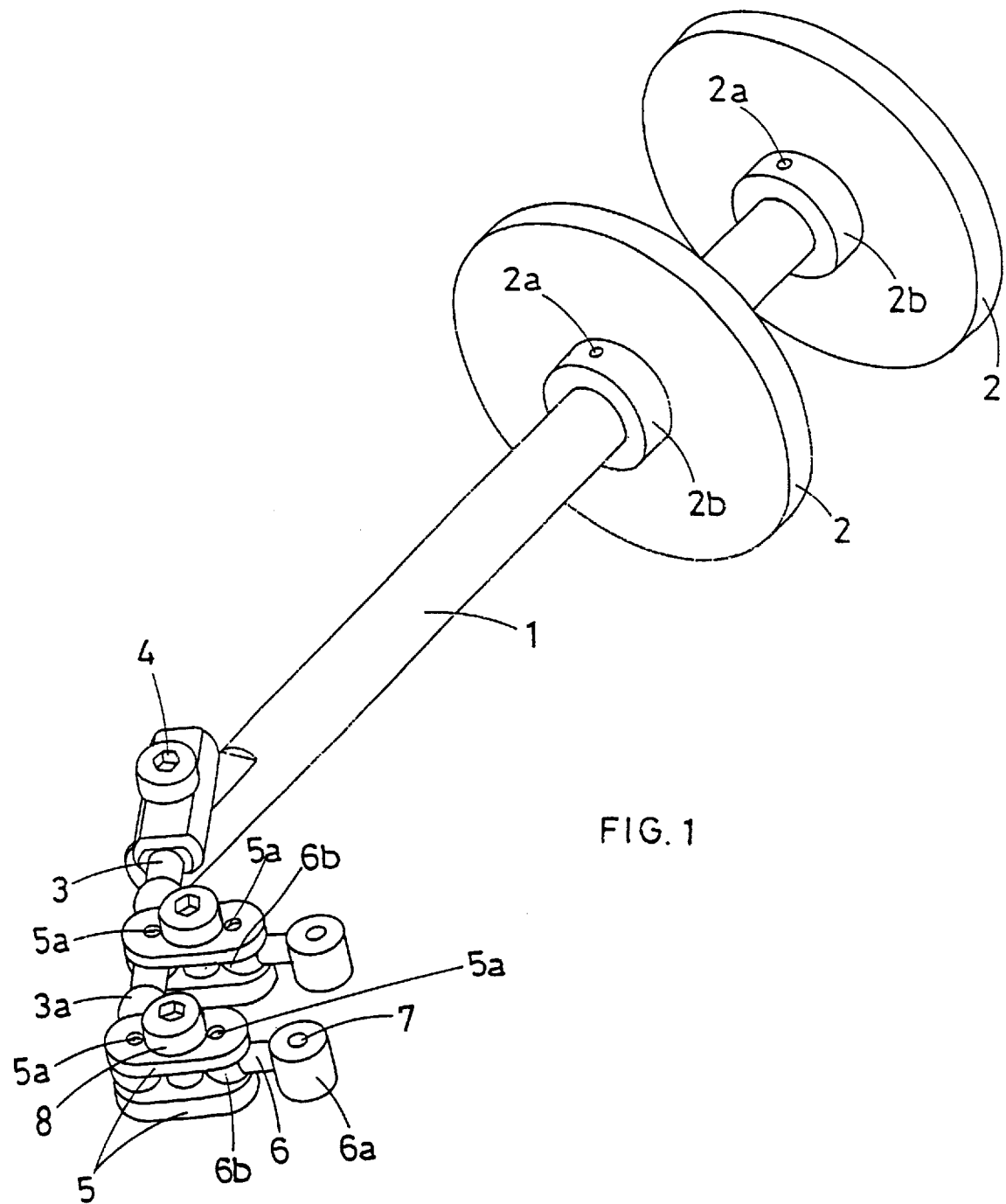
FIG. 1 is an axonometric view of the surgical instrument according to the present invention.

With reference to the enclosed figures, the surgical instrument according to the present invention comprises a handle made up of a rod (1) on which a close pair of disks (2) is fixed at an adjustable distance by means of two tightening nuts (2a) screwed on the two collars (2b) provided for each disk (2).

A second rod (3) is pivoted at the end of the rod (1) by means of a coupling tightening bolt (4).

The second rod (3) is characterized in that it comprises a regularly spaced series of small spheres (3*a*).

The instrument according to the present invention is also provided with two identical pairs of small plates (5), each of them acting as support for an element (6) ending with a head (6*a*) provided with a calibrated through hole (7).

At the other end the element (6) terminates with a small sphere (6*b*) perfectly identical in size to the small spheres (3*a*).

Each plate (5) features a pair of small ending holes (5*a*) or a central hole in which a bolt (8) is screwed in order to tighten the small spheres (3*a*) and the spheres (6*b*) inside the pair of plates (5).

What is claimed is:

1. A surgical instrument for drilling parallel holes for dental implants comprising a handle having a first rod having a pair of disks, each disk having a collar, said disks are adjustably spaced from each other on said first rod and secured by a tightening nut on each collar, a second rod pivotally mounted at the end of the first rod by means of a coupling and tightening bolt, said second rod has a regularly spaced series of small spheres and two or more identical pairs of plates, each plate featuring a pair of small ending holes and a central hole in which a bolt is screwed to allow for tightening of the plates of each pair, one against the other; and two or more elements, one for each pair of plates, ending with a head that has a calibrated through hole at one end of the element and a sphere at the other end, said sphere is identical in size to the spheres on said second rod.

* * * * *